United States Patent
Momose (10) Patent No.: US 11,644,430 B2
(45) Date of Patent: May 9, 2023

(54) RADIOGRAPHIC IMAGING DEVICE

(71) Applicant: Tohoku University, Sendai Miyagi (JP)

(72) Inventor: Atsushi Momose, Sendai (JP)

(73) Assignee: Tohoku University, Sendai-shi (JP)

( * ) Notice: Subject to any disclaimer, the term of this patent is extended or adjusted under 35 U.S.C. 154(b) by 0 days.

(21) Appl. No.: 17/419,143

(22) PCT Filed: Jan. 24, 2020

(86) PCT No.: PCT/JP2020/002457
§ 371 (c)(1),
(2) Date: Jun. 28, 2021

(87) PCT Pub. No.: WO2020/166304
PCT Pub. Date: Aug. 20, 2020

(65) Prior Publication Data
US 2022/0113264 A1    Apr. 14, 2022

(30) Foreign Application Priority Data
Feb. 15, 2019    (JP) .............................. JP2019-025006

(51) Int. Cl.
*G01N 23/041*    (2018.01)
*G01T 7/00*    (2006.01)
(52) U.S. Cl.
CPC ............. *G01N 23/041* (2018.02); *G01T 7/00* (2013.01)
(58) Field of Classification Search
CPC ............... G01N 23/041; G01N 23/083; G01N 23/20075; G01T 7/00; H01J 35/08; G06T 7/0012; G06T 7/11
See application file for complete search history.

(56) References Cited

U.S. PATENT DOCUMENTS 5,812,629 A    9/1998 Clauser
2005/0286680 A1    12/2005 Momose

FOREIGN PATENT DOCUMENTS

| EP | 3 598 115 A1 | 1/2020 |
| JP | 2012-13557 A | 1/2012 |
| JP | 2012013557 A * | 1/2012 |

(Continued)

OTHER PUBLICATIONS

Translation of JP2012013557 (Year: 2012).*
International Search Report for Application No. PCT/JP2020/002457 dated Mar. 24, 2020, 4 pgs.

*Primary Examiner* — David P Porta
*Assistant Examiner* — Mamadou Faye
(74) *Attorney, Agent, or Firm* — Seed Intellectual Property Law Group LLP (57) ABSTRACT

A high-sensitive phase imaging is achieved using a grating section without upsizing the imaging device or narrowing the period of the gratings. A radiation source generates radiation on a radiation path toward the grating section. The grating section comprises a G1 grating and a refraction-enhancing grating. The G1 grating has a G1 periodic structure that forms radiation converging points where an intensity of the radiation is increased between the G1 grating and a detector. The refraction-enhancing grating is located at the position of the radiation converging points and has enhancement planes and that increase the refraction angle of the radiation. The detector detects the radiation that has passed through the grating section.

10 Claims, 4 Drawing Sheets (56) References Cited

FOREIGN PATENT DOCUMENTS

| | | |
|---|---|---|
| JP | 2014-190778 A | 10/2014 |
| WO | 2004/058070 A1 | 7/2004 |
| WO | 2018/168621 A1 | 9/2018 |

* cited by examiner

RADIOGRAPHIC IMAGING DEVICE

BACKGROUND

Technical Field

The present disclosure relates to technology for observing the internal structure of a sample with high sensitivity, utilizing wave properties of radiation that has passed through the sample (subject), such as X-rays.

Description of the Related Art

Radiation of high penetrating power, such as X-rays, is widely used as a probe for observing the inside of an object in medical image diagnosis, non-destructive testing, security checking, etc. With regard to contrast of a fluoroscopic image, an object that strongly absorbs X-rays is depicted as an X-ray shadow, due to differences in X-ray attenuation coefficient.

X-ray absorption becomes stronger for objects that contain more elements with higher atomic numbers. Conversely, for a material that is made up of elements of lower atomic numbers, it can also be pointed out that it is difficult to obtain contrast, and this is a disadvantage of fluoroscopic images in principle. It is therefore not possible to obtain sufficient sensitivity to soft biological tissue, organic material, etc.

On the other hand, a method for overcoming the above-mentioned problem by using phase contrast of radiation, such as X-rays and neutrons, is known. As an approach for realizing a high sensitivity imaging method that uses phase contrast, a method that uses transmission gratings has been proposed (refer to patent publications 1 and 2 indicated below). An intensity pattern is formed on an image detector by radiation that has passed through transmission gratings aligned appropriately, and an object changes in accordance with slight refraction and scattering of radiation by the object. It is possible to obtain contrast that represents the structure of the object by this phenomenon. Absorption images corresponding to conventional images, refraction images that show magnitude of X-ray refraction by the object, and scattering images that show magnitude of scattering by the object, are generally produced by this method.

A typical configuration that uses transmission gratings is known as a Talbot interferometer. A Talbot interferometer consists of two transmission gratings, which are aligned by taking account of the Talbot effect. Phase contrast is obtained by detecting and processing moiré patterns that appear in the image of radiation through the two transmission gratings. Of the two transmission gratings, the one on the upstream side is called G1 and the one on the downstream side is called G2. An amplitude-type grating is used for G2, and a phase-type or amplitude-type grating is used for G1. A sample (subject) to be inspected is located normally upstream of G1. However, it is also possible to place the subject between G1 and G2, although there is a difference in imaging sensitivity.

In operating a Talbot interferometer, radiation with a partial spatial coherency (that is, radiation with well-ordered waves) should be used. As X-ray sources that satisfy this demand, there are synchrotron radiation sources and microfocus X-ray tubes. Since synchrotron radiation is generated at huge facilities, there are many restrictions in installation conditions. A microfocus X-ray tube has an advantage that it can be operated in laboratories, but its output power is limited. A widely-used conventional X-ray tube with a normal focus size has a large focus and a high output power, allowing a short exposure time. However, it cannot be used for a Talbot interferometer because it does not satisfy the demand of coherency.

A Talbot-Lau interferometer is known as a method that generates phase contrast by the principle of the Talbot interferometer even with a conventional X-ray tube with a normal focal size. A Talbot-Lau interferometer is constructed by placing a third transmission grating G0 near an X-ray tube and combining with a Talbot interferometer (G1 and G2). G0 is an amplitude type grating. X-ray phase imaging with a shortened exposure time is feasible by the Talbot-Lau interferometer, and applications to medical imaging systems and non-destructive testing are greatly expected.

It is not normal to use an intensity pattern (or moiré pattern) recorded by a detector as it is. Recorded images are processed by a computer according to a specific procedure, and then an absorption image, a refraction image, and a scattering image are generated and utilized. For this purpose, a fringe-scanning method is normally used. The fringe-scanning method is a method in which one of the transmission gratings is displaced in the direction of its period, a plurality of intensity patterns (or moiré patterns) are acquired, and image calculations are performed. More specifically, one of the transmission gratings is displaced by a distance of 1/K of its period d and an exposure is performed, and image calculation is performed from K images obtained by repeating this procedure. K is an integer equal to or larger than 3.

CITATION LIST

Patent Literature

[Patent publication 1] WO2004/058070
[Patent publication 2] U.S. Pat. No. 5,812,629

BRIEF SUMMARY

Technical Problem

Radiation has a property to penetrate straight into materials. However, considering the wave property of radiation, strictly speaking, radiation beams are bent by refraction at materials. This refraction is the signal used in phase imaging based on phase contrast. In the case of hard X-rays, the angle of beam deflection by refraction is normally below a microradian, and the sensitivity of phase imaging depends on how sensitively the beam deflection is detected.

Figure 1:
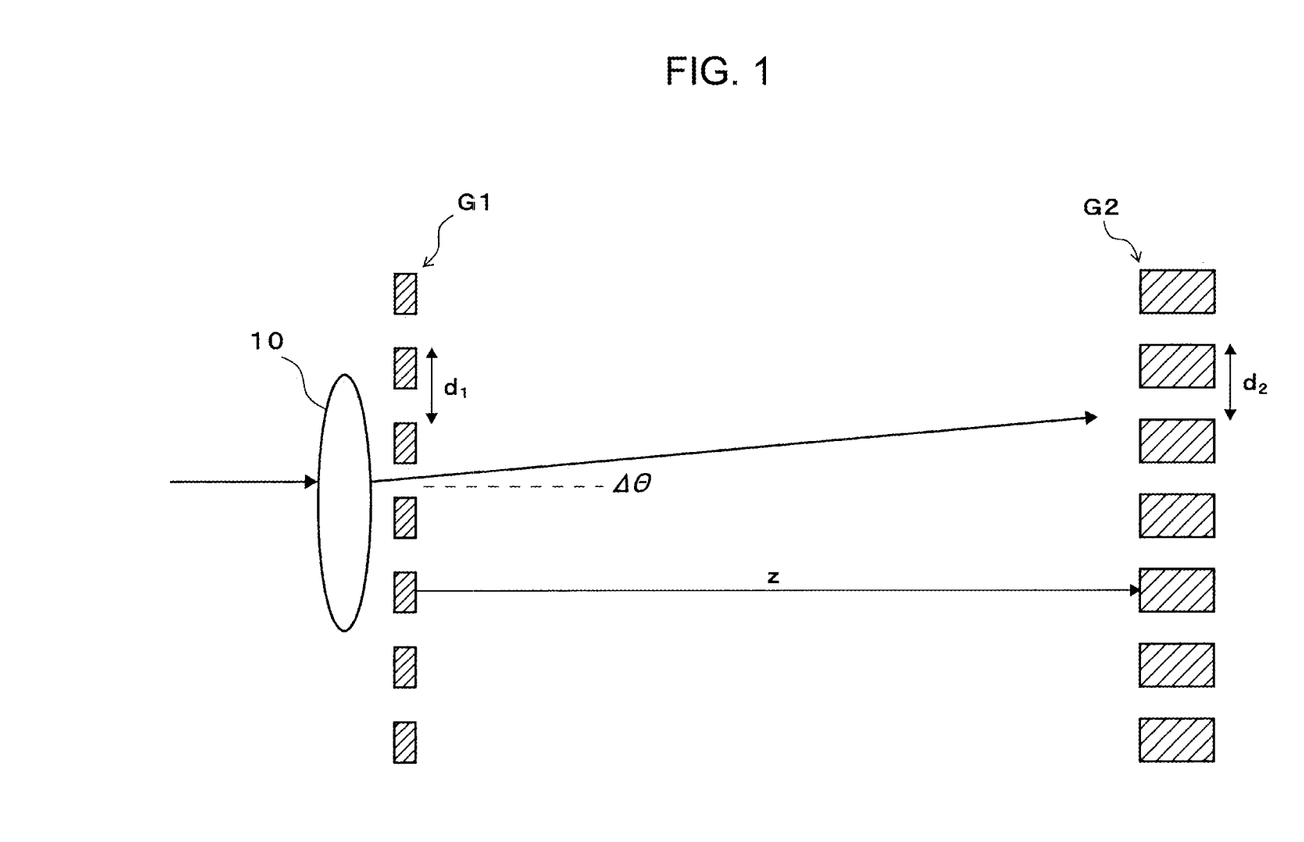
FIG. 1 is an explanatory drawing showing that radiation is refracted by a sample in a conventional radiographic imaging device.
Figure 2:
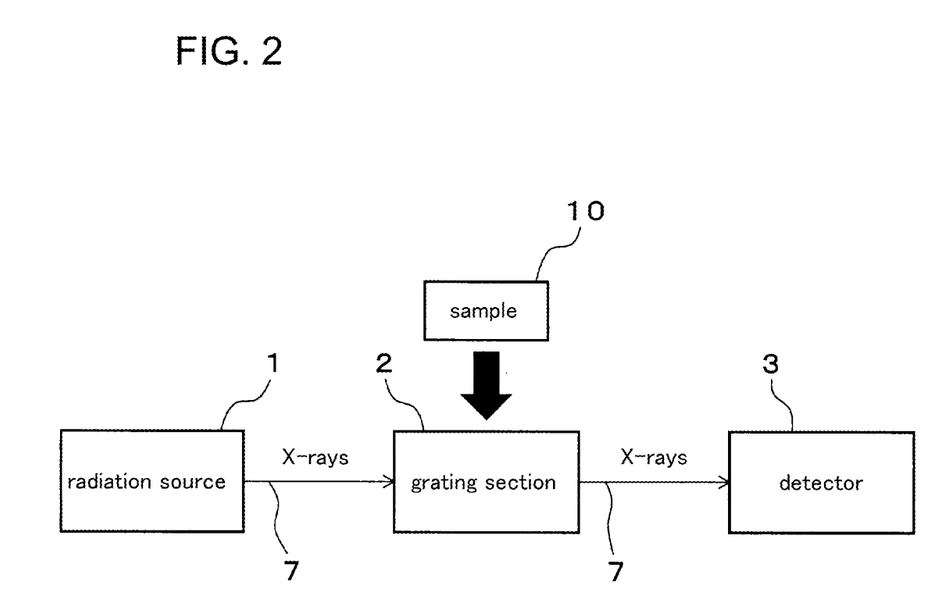
FIG. 2 is a block diagram showing the schematic structure of a radiographic imaging device of one embodiment of the present disclosure.

In general, an object is placed just upstream of G1. As shown in FIG. 1, given z as the distance between G1 and G2 and $d_2$ as the period of G2, the sensitivity S to the refraction is proportional to $z/d_2$. Therefore, the larger the G1-G2 distance is and the smaller $d_2$ is, the higher the sensitivity is. In FIG. 1, reference numeral 10 indicates a subject (sample).

In constructing a Talbot interferometer, $$z = p\frac{d_1 d_2}{\lambda} \qquad (1)$$

is satisfied, where $\lambda$ is the X-ray wavelength (when continuous X-rays are used, its central wavelength is used approximately), $d_1$ is the period of G1, and p is a half integer when a π/2 phase grating is employed for G1 and an odd multiple of ⅛ when a π phase grating is employed for G1. Then, the sensitivity S is expressed as $$S \propto \frac{pd_1}{\lambda} \quad (2)$$

Thus, to increase the sensitivity in the conventional configuration,
enlarging z by upsizing an interferometer system, or
reducing $d_1$ by developing a short period grating that is a hard challenge (this also implies making $d_2$ small),
is required. Therefore, in improving the sensitivity, there are problems of increasing device installation space or increasing costs for device development and manufacturing.

The present disclosure has been conceived based on the above described circumstances. The present disclosure provides technology that is capable of overcoming these problems.

Solution to Problem

Embodiments of the present disclosure can be described in the following aspects.
Aspect 1
A radiographic imaging device having gratings, which generates images by mapping refraction, scattering, and/or absorption of radiation caused by a sample, includes a radiation source, a grating section, and a detector. The radiation source generates radiation on a radiation path toward the grating section. The grating section comprises a G1 grating and a refraction-enhancing grating. The G1 grating has a G1 periodic structure for forming radiation converging points between the G1 grating and the detector. The refraction-enhancing grating is placed at the radiation converging points and has an enhancement plane that enhances the refraction. The detector is configured to acquire images of the radiation that has passed through the grating section.
Aspect 2
The radiographic imaging device described in aspect 1, wherein the enhancement plane has parabolic sections whose apexes are placed at the position of the radiation converging points in the absence of the sample.
Aspect 3
The radiographic imaging device described in aspect 1 or aspect 2, wherein multiple enhancement planes are aligned along the radiation path so that the radiation is refracted one by one.
Aspect 4
The radiographic imaging device described in any one of aspect 1 to aspect 3, wherein the G1 periodic structure comprises periodically arranged concave parts.
Aspect 5
The radiographic imaging device described in aspect 4, wherein the concave parts are elliptical cross sections.
Aspect 6
The radiographic imaging device described in any one of aspect 1 to aspect 5, wherein the grating section further comprises a G2 grating; the G2 grating has a G2 periodic structure, which has a period almost comparable to the period of the self-image of the G1 grating formed at the position of the G2 grating by the radiation that has passed through the refraction-enhancing grating and the G1 grating; and the detector is configured to acquire the self-image behind the G2 grating.

Aspect 7
The radiographic imaging device described in any one of aspect 1 to aspect 6, wherein the enhancement plane has parabolic sections that substantially satisfy Equation 3:

$$y = \frac{M-1}{\delta z} x^2 \quad (3)$$

where
x is a coordinate perpendicular to the radiation path,
y is a coordinate parallel with the radiation path,
z is a distance from the G1 grating to the refraction-enhancing grating,
δ is δ when the refractive index of the refraction-enhancing grating having the enhancement plane is given by 1-δ, and
M is an enhancement factor of refraction by the refraction-enhancing grating.
Aspect 8
The radiographic imaging device described in any one of aspect 1 to aspect 7, wherein the radiation converging points are areas where the radiation intensities are increased and the areas are formed between the position where the size of the converging points is minimum and the G1 grating.
Aspect 9
A grating section, which generates images by mapping refraction, scattering, and/or absorption of radiation caused by a sample, comprising a G1 grating and a refraction-enhancing grating, wherein the G1 grating has a G1 periodic structure to form radiation converging points where an intensity of radiation irradiated on the G1 grating is increased, and the refraction-enhancing grating is placed at a position of the radiation converging points and has enhancement planes that enhance a refraction of the radiation.
Aspect 10
A radiographic imaging method using a grating section, which generates images by mapping refraction, scattering, and/or absorption of radiation caused by a sample, wherein the grating section comprises a G1 grating and a refraction-enhancing grating, the G1 grating has a G1 periodic structure for forming radiation converging points, and the refraction-enhancing grating is placed at the radiation converging points and has enhancement planes that enhance the refraction, the method comprising a step of irradiating the radiation on the grating section, a step of forming the radiation converging points by the G1 grating, a step of enhancing the refraction by the enhancement planes of the refraction-enhancing grating at the position of the radiation converging points, and a step of detecting the radiation that has passed the grating section.

Advantageous Effect of the Disclosure

According to the present disclosure, it is possible to perform highly sensitive X-ray phase imaging without the need to upsize the device and/or reducing the grating period.

DETAILED DESCRIPTION

Structure of Embodiment

In the following, a radiographic imaging device (hereafter sometimes referred to as "device") of an embodiment of the present disclosure will be described with reference to attached figures. This device generates images by mapping refraction, scattering, and/or absorption of radiation caused by a sample by using gratings. A living body or a non-living body is used as a sample. This device is used for medical or non-medical purposes. Examples of non-medical applications include, but are not limited to, non-destructive testing of foods, industrial parts, and industrial products.

The device of this embodiment comprises a radiation source 1, a grating section 2, and a detector 3 as fundamental components (see FIG. 1).

Radiation Source

The radiation source 1 generates radiation 7 toward the grating section 2. The radiation source 1 used in this embodiment can generate radiation with a degree of spatial coherency sufficient for generating a clear self-image by the G1 grating 21 (mentioned below) of the grating section 2. This requires that the waves of the radiation are well-ordered, and for example when X-rays are used as radiation, a synchrotron radiation source or a micro-focus X-ray tube is available as the radiation source 1. Hereafter, an embodiment using a micro-focus X-ray tube as the radiation source 1 is described.

Grating Section

Figure 3:
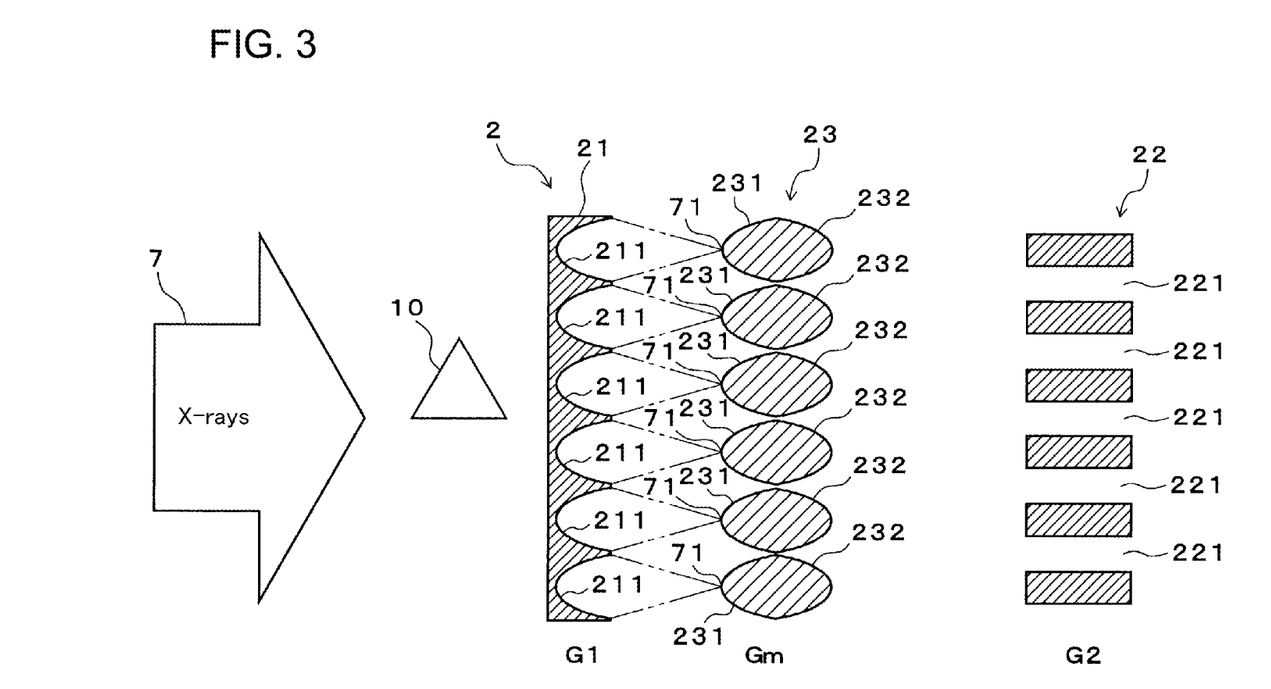
FIG. 3 is an explanatory drawing showing the structure of a grating section used for the device shown in FIG. 2.

The grating section 2 comprises a G1 grating 21, a G2 grating 22, and a refraction-enhancing grating 23 (see FIG. 3).

The G1 grating 21 has periodically formed concave parts 211. These concave parts 211 have a G1 periodic structure to form radiation converging points 71 between the G1 grating 21 and the detector 3, where the intensity of the radiation 7 is increased. The concave parts 211 in this embodiment have elliptical cross sections (see FIG. 3). In FIG. 3, the convergences of the radiation 7 are illustrated by two-dot chain lines.

The refraction-enhancing grating 23 is placed at the position where the radiation converging points 71 are formed. The refraction-enhancing grating 23 has a first enhancement plane 231 and a second enhancement plane 232 that increase the refraction angle of the radiation 7.

The first enhancement plane 231 and the second enhancement plane 232 in this embodiment have parabolic cross sections (see FIG. 3). Here, the first enhancement plane 231 and the second enhancement plane 232 may have paraboloids of revolution. The positions of the apexes of the parabolas of the first enhancement plane 231 and the second enhancement plane 232 correspond to the positions of the radiation converging points 71 of the radiation 7 in the absence of a sample 10. FIG. 3 shows a drawing in which the distance between gratings in the y direction (parallel with the path of radiation 7) is reduced, and the radiation converging points 71 are actually stretched in the y direction. More details are described later.

In this embodiment, since the first enhancement plane 231 and the second enhancement plane 232 are made together on the refraction-enhancing grating 23, multiple enhancement planes are aligned along the radiation 7 and refract the radiation 7 sequentially. The function of the enhancement planes is described below.

The G2 grating 22 has multiple slits 221 arranged periodically. The G2 grating 22 in this embodiment has a G2 periodic structure formed by the slits 221.

The G2 periodic structure of the G2 grating 22 has a period almost comparable to the period of the self-image of the G1 grating 21 formed by the radiation 7 that has passed through the G1 grating 21 and the refraction-enhancing grating 23 at the position of the G2 grating 22. The G2 grating 22 can be displaced with a step of $d_2/K$ by a translation mechanism (not shown). Here, $d_2$ is the period of the G2 grating 22, and K is an integer equal to or larger than 3. Otherwise, the G1 grating 21 and the refraction-enhancing grating 23 may be displaced synchronously by steps of $d_1/K$ and $d'_1/K$, respectively, where $d'_1$ is the period of the refraction-enhancing grating 23. The grating translation mechanism is the same as that used for a conventional fringe-scanning method, and its details are omitted.

The position of the G2 grating 22 can be at positions where the self-images of the G1 grating 21 are formed. In this embodiment, the position of the G2 grating 22 is determined by considering the condition that the radiation that has passed through the G1 grating 21 further passes through the refraction-enhancing grating 23. Because there is a possibility of shape errors in artificially fabricated gratings, the position of the G2 grating 22 may also be determined experimentally by examining the position where the visibility of observed moiré pattern is high.

The grating section 2 in this embodiment is configured as a so-called Talbot interferometer consisting of the G1 grating 21 and the G2 grating 22, but the present disclosure is not limited to this, and it is also possible to omit the G2 grating 22 and acquire self-images of the G1 grating 21 by the detector 3 directly.

Here, the parabolic cross section of the first enhancement plane 231 and the second enhancement plane 232 in this embodiment substantially satisfies Equation (3) below. 'Substantially' implies that approximated shapes available for practical uses are involved.

$$y = \frac{M-1}{\delta z} x^2 \qquad (3)$$

where x is a coordinate perpendicular to the radiation path, y is a coordinate parallel with the radiation path, z is a distance from the G1 grating to the refraction-enhancing grating, δ is δ when the refractive index of the refraction-enhancing grating having the enhancement plane is given by 1-δ, and M is an enhancement factor of refraction by the refraction-enhancing grating (M>1).

Detector

The detector 3 records the self-image of the G1 grating 21 as a moiré pattern through the G2 grating 22. When the G2 grating 22 is not used, the self-image of the G1 grating 21 is recorded directly. Furthermore, when the G2 grating 22 is used, the detector 3 acquires K moiré patterns (K is an integer equal to or larger than 3) associated with the displacement of the G2 grating 22, and desired radiographic images are generated through the normal procedure of the phase imaging by the fringe-scanning method. The detector 3 for this purpose is the same as conventional methods, and more details are omitted.

Radiographic Image Generation Method in this Embodiment

Figure 4:
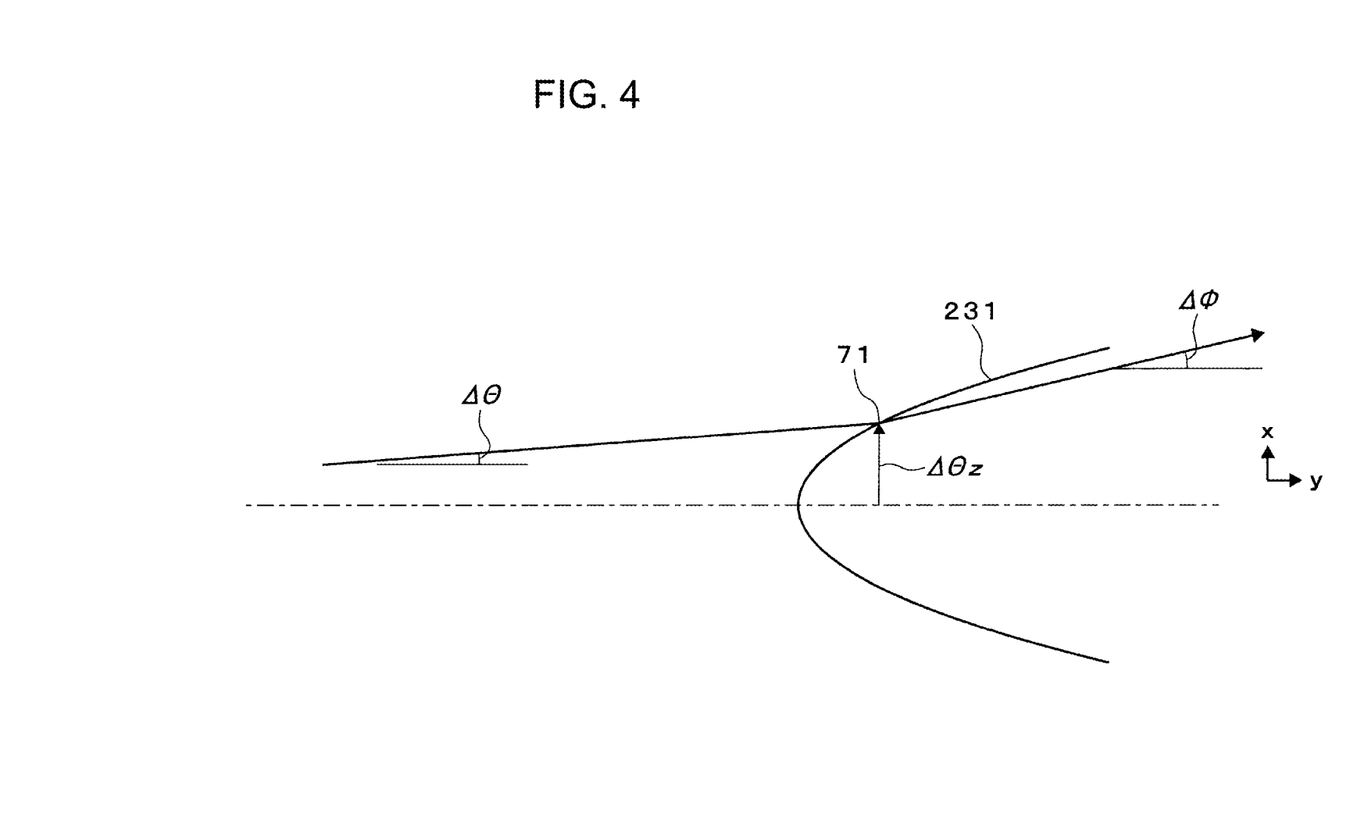
FIG. 4 is an explanatory drawing showing the function of refraction enhancement by a refraction-enhancing grating.

The radiographic image generation method by using the above-mentioned device is described with reference to FIGS. 3 and 4.

First, the sample 10 is placed upstream of the G1 grating 21 (see FIG. 3).

Next, as shown in FIG. 3, the radiation 7 is generated toward the sample 10 and the G1 grating 21. Then, the radiation 7 passes through the G1 grating 21, and the radiation converging points 71 of the radiation 7 are formed.

Here, assuming that the radiation 7 is deflected by AO by the sample 10 (see FIG. 4), the position of the radiation converging points 71 (that is, the focusing points of the radiation) are displaced by $\Delta\theta \cdot z$ laterally and hit on the positions shifted from the apexes of the first enhancement plane 231. Here, the radiation 7 is refracted in accordance with the Snell's law and the propagation direction of the radiation is increased to $\Delta\phi$ (see FIG. 4). As mentioned, the position of the radiation converging points 71 spans in a long range along the propagation direction, and rays reaching the radiation converging points 71 are drawn by single lines in FIG. 4.

At the second enhancement plane 232, the same phenomenon as that of the first enhancement plane 231 occurs. In this embodiment, the second enhancement plane 232 is made in the refraction-enhancing grating 23, and therefore the enhancement of the refraction by the refraction-enhancing grating 23 is twice of that by a single enhancement plane; that is, 2M-fold enhancement is expected in this embodiment.

As mentioned, the radiation converging points 71 have shapes stretched along the propagation direction of the radiation 7 in general. In other words, its focal depth is large. For example, in the case of X-rays, the depth is more than a thousand times of the period of the G1 periodic structure. Therefore, it is considered that the spot sizes of the radiation converging points 71 are constant both at the first enhancement plane 231 and the second enhancement plane 232, and the same refraction effects are expected.

The detector 3 detects the radiation that has passed through the G2 grating 22. Phase imaging in a conventional manner is possible. Here, in this embodiment, multiple images are acquired by displacing the G2 grating 22 with a predetermined pitch and performing exposures. When the G2 grating 22 is not used, multiple images are acquired by displacing the G1 grating 21 and the refraction-enhancing grating 23 synchronously with a predetermined pitch and performing exposures. Required phase images (absorption image, refraction image, and/or scattering image) are generated from these multiple images. The calculation procedure of these images follows the conventional one, and more details are omitted.

By the device of this embodiment, the deflection angle AO by the refraction at the sample 10 is enhanced to $\Delta\phi$, which corresponds to M times of AO. Therefore, without upsizing the device or shortening the grating period, the sensitivity of phase imaging can be increased.

The description of this embodiment is only illustrative and does not show an essential configuration of the present disclosure. The constitution of each component does not limited to the above description as long as it falls within the scope of the present disclosure.

For example, although an X-ray tube was employed for the radiation source 1, another radiation that has a power to penetrate the sample 10, such as a neutron source, may be used. In this case, a detector that can detect the radiation used is employed. With regard to the gratings, gratings comprising materials that change the phase of the radiation used, materials that attenuate the intensity of the radiation used, and materials that refract the radiation used are employed depending on usage.

In the above-mentioned embodiment, while the cross section of the G1 periodic structure along the direction of its period consists of parabolic sections, it is also possible to select other section shapes, such as elliptical sections or triangular sections. In short, any G1 periodic structures that are capable of forming radiation converging points 71 of the radiation 7 can be used. Elliptical sections are especially preferable because the size of radiation converging points 71 (spot size) are minimized.

Moreover, in the above-mentioned embodiment, the first enhancement plane 231 and the second enhancement plane 232 are formed on a single refraction-enhancing grating 23, but only one of the enhancement planes can be formed on the refraction-enhancing grating 23. In such a case, the opposite plane of the enhancement plane of the refraction-enhancing grating 23 can have a shape that does not affect the refraction-enhancing effect, such as a flat shape.

Furthermore, in the above-mentioned embodiment, a single refraction-enhancing grating 23 is placed, but it is possible to gain a more refraction-enhancing effect by placing two or more refraction-enhancing gratings along the radiation propagation direction so that the radiation passes through them sequentially. Provided that the converging points span all enhancing planes, a N×M refraction enhancing gain is expected by using N refraction-enhancing gratings.

Also, it is possible to suppress the absorption of the radiation by the refraction-enhancing grating 23 by making hollows in the internal region of the refraction-enhancing grating 23. It is also possible to suppress the absorption of the radiation by the refraction-enhancing grating 23 by dividing the enhancement plane and constituting a plate-like form, like a kinoform lens or a Fresnel lens.

In FIG. 3, the G1 grating 21, the G2 grating 22, and the refraction-enhancing grating 23 are separated, but it is also possible to constitute these gratings monolithically by fabricating them from a single substrate.

It is also possible to construct a Talbot-Lau interferometer by adding a G0 grating (not shown) to the above-mentioned embodiment. It is desirable to determine the period of the G0 grating so that the converging points of the radiation 7 are located at the position of the refraction enhancing grating 23 and the self-image of the G1 grating 21 is formed at the position of the G2 grating 22.

In FIG. 3, a one-dimensional grating structure that has a periodic structure in one direction is illustrated, and it is also possible in this embodiment to use a two-dimensional grating that has a periodic structure in two directions. In this case, paraboloids of revolution are desirable for the enhancement planes of the refraction-enhancing grating.

The converging points in this embodiment imply the areas where the intensity of the radiation 7 is more increased than that just in front of the G1 grating 21. For instance, the converging points in this embodiment can be assigned at any positions between the G1 grating 21 and the position where the spot size (the size of converging radiation) of the radiation 7 is minimum. The refraction-enhancing effect is expected by placing the refraction-enhancing grating 23 even at these positions where the radiation intensity is locally increased (focused) by the G1 grating 21.

DESCRIPTION OF THE REFERENCE NUMERALS 1 radiation source
2 grating section
21 G1 grating
211 concave part
22 G2 grating
221 slit
23 refraction enhancing grating
231 first enhancement plane
232 second enhancement plane
3 detector
7 radiation
71 converging point
10 sample The various embodiments described above can be combined to provide further embodiments. All of the patents, applications, and publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A radiographic imaging device having gratings, which generates images by mapping refraction, scattering, and/or absorption of radiation caused by a sample, comprising:
    a radiation source,
    a grating section, and
    a detector,
    wherein:
        the radiation source generates radiation on a radiation path toward the grating section;
        the grating section comprises a G1 grating and a refraction-enhancing grating;
        the G1 grating has a G1 periodic structure for forming radiation converging points between the G1 grating and the detector;
        the refraction-enhancing grating is placed at the radiation converging points and has an enhancement plane that enhances a refraction of the radiation;
        the enhancement plane has parabolic sections, whose apexes are placed at the radiation converging points in the absence of the sample; and
        the detector is configured to acquire images of the radiation that has passed through the grating section.

2. The radiographic imaging device of claim 1, wherein multiple enhancement planes are aligned along the radiation path so that the radiation is refracted one by one.

3. The radiographic imaging device of claim 1, wherein the G1 periodic structure comprises periodically arranged concave parts.

4. The radiographic imaging device of claim 3, wherein the concave parts are elliptical cross sections.

5. The radiographic imaging device of claim 1, wherein:
    the grating section further comprises a G2 grating;
    the G2 grating has a G2 periodic structure, which has a period almost comparable to the period of a self-image of the G1 grating formed at the position of the G2 grating by the radiation that has passed through the refraction-enhancing grating and the G1 grating; and
    the detector is configured to acquire the self-image behind the G2 grating.

6. The radiographic imaging device of claim 1, wherein the parabolic sections of the enhancement plane substantially satisfy Equation 3:

$$y = \frac{M-1}{\delta z} x^2 \qquad (3)$$

where
    x is a coordinate perpendicular to the radiation path,
    y is a coordinate parallel with the radiation path,
    z is a distance from the G1 grating to the refraction-enhancing grating,
    δ is δ when the refractive index of the refraction-enhancing grating having the enhancement plane is given by 1-δ, and
    M is an enhancement factor of refraction by the refraction-enhancing grating.

7. The radiographic imaging device of claim 1, wherein the radiation converging points are areas where the radiation intensities are converged and the areas are formed between the position where a size of the radiation converging points is minimum and the G1 grating.

8. A grating section, which generates images by mapping refraction, scattering, and/or absorption of radiation caused by a sample, comprising:
    a G1 grating; and
    a refraction-enhancing grating,
    wherein:
        the G1 grating has a G1 periodic structure to form radiation converging points where an intensity of radiation irradiated on the G1 grating is increased,
        the refraction-enhancing grating is placed at a position of the radiation converging points and has enhancement planes that enhance a refraction of the radiation, and
        the enhancement planes have parabolic sections, whose apexes are placed at the radiation converging points in the absence of the sample.

9. A radiographic imaging method using a grating section, which generates images by mapping refraction, scattering, and/or absorption of radiation caused by a sample, wherein the grating section comprises a G1 grating and a refraction-enhancing grating, the G1 grating has a G1 periodic structure for forming radiation converging points, and the refraction-enhancing grating is placed at the radiation converging points and has enhancement planes that enhance a refraction of the radiation, the method comprising:
    irradiating the radiation on the grating section,
    forming the radiation converging points by the G1 grating,
    enhancing the refraction by the enhancement planes of the refraction-enhancing grating at the radiation converging points, wherein the enhancement planes have parabolic sections, whose apexes are placed at the radiation converging points in the absence of the sample, and detecting the radiation that has passed the grating section.

10. The radiographic imaging device of claim 1, wherein the refraction-enhancing grating is separately disposed with having a distance from the G1 grating, and the enhancement plane is disposed at one or more of the radiation converging points.

* * * * *